United States Patent [19]

Driver

[11] Patent Number: 4,612,725
[45] Date of Patent: Sep. 23, 1986

[54] METHOD FOR ACCLIMATIZING AND PROPAGATING PLANT TISSUE CULTURE SHOOTS

[75] Inventor: John A. Driver, Modesto, Calif.

[73] Assignee: Plant Research Laboratories, Modesto, Calif.

[21] Appl. No.: 740,778

[22] Filed: Jun. 3, 1985

[51] Int. Cl.⁴ .......................... A01H 3/04; A01C 1/00
[52] U.S. Cl. ...................................................... 47/58
[58] Field of Search ................ 47/29, 58, DIG. 4, 28; 435/420, 421

[56] References Cited

U.S. PATENT DOCUMENTS

| | | | |
|---|---|---|---|
| 3,384,992 | 5/1968 | Heffron | 47/29 |
| 3,816,960 | 6/1974 | Gudin et al. | 47/58 |
| 4,003,156 | 1/1977 | Sibi et al. | 435/240 |
| 4,217,730 | 8/1980 | El-Nil | 435/240 |
| 4,353,184 | 10/1982 | El-Nil | 435/240 |
| 4,463,522 | 8/1984 | Lindemann | 435/240 |
| 4,532,733 | 8/1985 | Krul | 47/58 |
| 4,548,901 | 10/1985 | Christianson et al. | 435/241 |

OTHER PUBLICATIONS

Jones, J. B. (1983) "Tissue Culture Takes Off"*Florists' Review* vol. 172 No. 4451, Mar. 24, 1983 pp. 29–34.
Hartmann, H. T., et al., (4th Ed) of *Plant Propagation* Pub. Prentice-Hall, Inc. 1983 pp. 532, 538, 545–550 and 569–580 relied on.
Driver et al. (1984) HortScience 19:507–509.
Broome et al. Cell Culture and Somatic Cell Gen. 1:111–121.
Dunstan et al. (1984) Cell Culture and Som. Cell Gen. 1:123–129.
Fuchigami et al. (1981) J. Amer. Soc. Hort. Sci. 106:519–522.
Brainerd et al. (1981) J. Amer. Soc. Hort. Sci. 106:515–518.
Tissue Culture Techniques, (Tissue Culture in Forestry) Bonga & Durzan eds. (1982).
Frontiers of Plant Tissue Culture (1978) "Physiological and Biochemical Aspects of Organogenesis In Vitro" T. A. Thorpe, 49–58.
Tissue Culture in Forestry (1982) "Carbohydrate Utilization And Metabolism" T. A. Thorpe, 325–368.
Advances in Cell Culture, vol. 1, "Regulation of Plant Organogenesis" T. A. Thorpe et al., (1981) 213–239.
M. Boulay (1979) French article "Propagation In Vitro . . . ".
Butcher et al. (1960) J. Exp. Botany 11:206–216.
Cheng et al. (1977) Science 198:306–307.
Feliciano et al. (1983) HortScience 18:705–706.
Greenwood et al. (1973) Amer. J. Bot. 60:42–47.
Hyndman et al. "A Basis for Increased . . . " 9 pages.
Miller et al. (1982) HortScience 17:194.
Maretzki et al. (1980) Oyton 38:85–88.
Minocha (1980) Can. J. Bot. 58:366–370.
Simmonds (1984) Plant Cell Tissue Culture 3:283–289.
Simmonds (1983) "Direct Rooting of Micro . . . " Elsevier 5 pages.
Sommer et al. (1981) Plant Tissue Culture, pp. 349–358.
Sriskandarajah et al. (1981) HortScience, 56:71–76.
Welander "Influence of Medium Composition . . . " 6 pages.

*Primary Examiner*—James R. Feyrer
*Attorney, Agent, or Firm*—Townsend & Townsend

[57] ABSTRACT

A method for the acclimatization of plant propagules obtained by tissue culture techniques allows the direct field rooting of the propagules. Tissue culture propagules are first treated under conditions which provide for hardening or lignification of the propagule prior to root induction. The hardened propagules are exposed to a root induction medium for a time sufficient to initiate root formation, but are removed from the medium prior to root emergence. The plantlets are then substantially immediately planted in the field where root formation occurs. Root formation in the field avoids root shock which may occur when plantlets are transplanted after root formation is accomplished under greenhouse conditions. The propagules which are planted in the field are protected by a light and moisture barrier which provides for controlled humidity, light intensity, and temperature conditions until the resulting plantlet is sufficiently acclimatized to survive in the uncontrolled environment.

28 Claims, 1 Drawing Figure

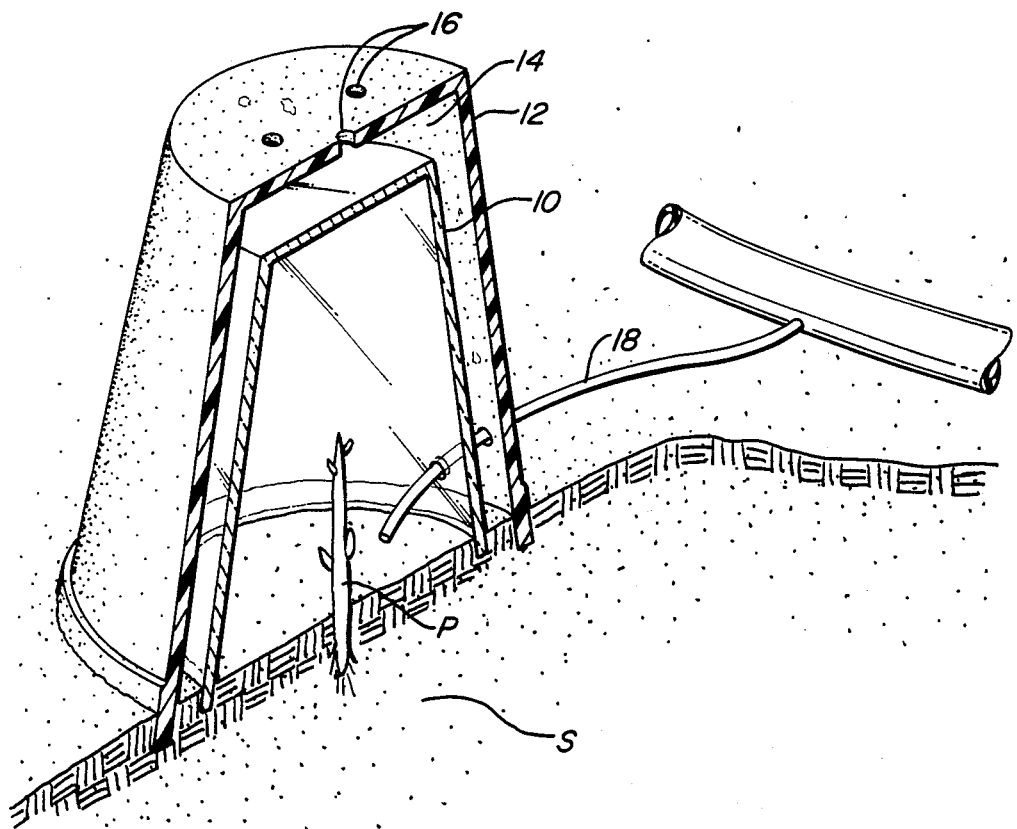
FIG._1.

METHOD FOR ACCLIMATIZING AND PROPAGATING PLANT TISSUE CULTURE SHOOTS

BACKGROUND OF THE INVENTION

1. Field of the Invention

The present invention relates generally to the asexual reproduction of higher plants, and more particularly to a method for acclimatizing plant propagules obtained by in vitro tissue culture methods and for planting the acclimatized propagules prior to root formation in the field.

Plant tissue culture refers to various methods which have been developed for asexually reproducing plants from juvenile and rejuvenated mature plant material. Typically, a shoot, shoot tip, bud, stem section, or stem base is excised from a growing plant, disinfested, and placed in appropriate hormone and nutrient solutions to cause auxillary growth and shoot lengthening in a multiplication culture to form multiple plant propagules. The advantage of such asexual reproduction is that mature plants having desirable characteristics can be replicated precisely if appropriate steps are taken.

Various methods are presently employed for the rooting and acclimatization of such tissue culture propagules. For example, rooted shoots from multiplication cultures may be transferred to individual containers having an appropriate potting mix and maintained in a greenhouse to allow gradual acclimatization. Humidity levels in the greenhouse are initially elevated but gradually reduced as the plantlet becomes acclimatized to the new environment. After sufficient acclimatization has occurred, the plantlet may be transferred to the field with a reasonable chance of survival. This approach, although workable for many plants, suffers from the need to employ the intermediate greenhouse acclimatization step which may last from 4 to 6 weeks, or longer. Such acclimatization in the greenhouse greatly increases the expense of producing the field plantlets, but heretofore has been considered necessary for the survival of many types of plants.

Field acclimatization of many plants has proved problematic even when great care is taken in making the transition from tissue culture to the field. For example, many woody tree species suffer from root acclimatization problems even when care is taken to acclimatize the shoot portion of the plantlet to ambient field conditions prior to planting.

For the above reasons, it would be desirable to provide an improved method for root induction and acclimatization of plant propagules obtained from tissue culture. It would be particularly desirable to provide such a method which would allow the direct field planting of such plant propagules prior to root formation to facilitate root acclimatization of the resulting plantlet.

2. Description of the Prior Art

The propagation of Paradox walnut root stock by shoot tip tissue culture is described in Driver and Kuniyuki (1984) Hort.Science 19:507–509. The method relies on multiple shoot formation resulting from the tissue culture of nodal explants in a suitable basal medium, followed by shoot formation in the presence of N6-benzyladenine and indole-3-butyric acid. An optimum medium for inducing multiple shoot formation of Paradox walnut is described and designated DKW. Root formation is induced in the presence of indole-3-butyric acid and naphthaleneacetic acid. Plantlets were grown from root shoots in a synthetic potting mix in a misting chamber over a 6 week period. Such plantlets were found able to withstand uncontrolled environmental conditions in small-scale trials.

The micropropagation of fruit trees and plants is discussed in the following references: Broome and Zimmerman, "Culture of Shoot Meristems: Fruit Plants," in *Cell Culture and Somatic Cell Genetics of Plants, Vol.* 1, Academic Press, Inc., New York, pp. 111–122; Dunstan and Turner, "The Acclimatization of Micropropagated Plants," in *Cell Culture and Somatic Cell Genetics of Plants, Vol.* 1, supra, pp. 123–129; Fuchigami et al. (1981) J. Amer. Soc. Hort. Sci. 106:519–522; and Brainerd and Fuchigami (1981) J. Amer. Soc. Hort. Sci. 106:515–518. See also *Tissue Culture and Forestry*, Bonga and Durzan, eds., Martinus Hijholf, Netherlands (1982), for a discussion of the micropropagation of other woody plants.

SUMMARY OF THE INVENTION

The present invention provides a method for the acclimatization and direct field rooting of plant propagules derived by tissue culture techniques. The method is characterized by initially placing the tissue culture propagules in a pretreatment medium having elevated sugar concentrations and reduced nitrogen salt concentrations (compared to conventional multiplication culture media), which causes lignification and hardening of the propagules. After sufficient lignification has occurred, the propagules are usually transferred to a rooting environment including root-inducing compounds, although for some species it will be possible to induce root formation during the pretreatment stage. The shoots are removed from the root-inducing environment after root initiation but prior to root emergence, and are then planted directly in the field where root formation occurs. Light and humidity conditions in the field are controlled to allow gradual acclimatization of the resulting plantlet to ambient conditions. Conveniently, the light and humidity conditions are controlled through use of a light and moisture barrier which is placed over the plantlet combined with proper irrigation. The method is useful for virtually all plant species capable of micropropagation in tissue culture, and is particularly useful for those species which have been recalcitrant to conventional acclimatization procedures.

BRIEF DESCRIPTION OF THE DRAWINGS

FIG. 1 is a sectional, perspective view of a plant cover suitable for use in the method of the present invention.

DESCRIPTION OF THE SPECIFIC EMBODIMENTS

According to the present invention, a wide variety of higher plant propagules which have been obtained by tissue culture methods may be acclimatized, and rooted in the field, without the need for an intermediate acclimatization period under greenhouse conditions. The elimination of the intermediate acclimatization step is made possible by initially treating the tissue culture propagules under conditions which provide for the hardening or lignification of the propagules prior to root induction. Such treatment has been found to predispose the propagule to organogenesis, i.e., the development of roots and leaves. After sufficient hardening is achieved in the initial treatment step, the propagules are usually exposed to a root induction medium and substantially immediately planted in the field. By planting the propagules prior to root emergence, root formation occurs in the field and root shock resulting from transplanting a young plantlet is avoided. Initially, the planted propagule is protected from the ambient environment by a moisture and light barrier which surrounds the plant in a high-humidity, reduced light intensity environment until it is able to survive without such protection.

The method of the present invention is applicable to a wide variety of plants which may be propagated from propagules obtained by tissue culture techniques from mature plant material. Suitable plants include woody plants, particularly dicotyledons, including both gymnosperms, such as forest tree species, and angiosperms, such as deciduous fruit and nut trees. The method is exemplified hereafter with experimental data demonstrating the successful propagation of walnut (Paradox walnut, *Juglans hindsii* $\times$ *J. regia*) and peach trees (*Prunus persica*), both of which species have heretofore required extensive greenhouse acclimatization prior to field planting.

Propagules suitable for propagation by the methods of the present invention may be obtained by conventional tissue culture techniques such as multiplication culture where whole plant material is obtained from a juvenile or rejuventated mature, growing plant, typically at a growing point or area of rapidly dividing cells at the tip of a stem, root or branch, referred to as meristem material or "shoots". The meristem material is placed in a predefined hormonal and nutritional medium, where auxillary shoots are formed. Multiplication culture media for a wide variety of plants are reported in the patent and scientific literature, and usually include a carbon source, such as sucrose or other sugars; a nitrogen source, such as ammonium and/or nitrate salts; potassium; phosphorous; micronutrients; and a solid media base such as agar or Gelrite ®. Individual shoots may be divided fom such multiplication cultures and treated by the methods described hereinbelow for regeneration of the whole plant. Such asexual reproduction of plants from a single parent allows cloning of plant progeny having identical genetic characteristics to those of the parent.

An optimum multiplication culture medium for the preparation of Paradox walnut propagules is described in Driver and Kuniyuki (1984), supra. Nodal explants from vigorously growing Paradox walnut seedlings are sterilized and placed in a basal medium without hormones (see formulation below). After approximately one week, viable propagules are selected and transferred to basal medium supplemented with approximately 4.5 $\mu$M N6-benzyladenine (BA), and approximately 5 nM indole-3-butyric acid (IBA). Light intensity during the multiplication stage is maintained at reduced levels, ususally about 50 $\mu Es^{-1}m^{-2}$, and the period of light exposure is 24 hours/day. Temperature is usually elevated at about 25°–30° C., more usually about 28° C. The propagules will form multiplication cultures characterized by a stable growth rate producing multiple shoots of sufficient size to be treated in accordance with the remaining steps of the present invention. Such multiplication cultures may be maintained indefinitely to provide a continuing source of viable propagules.

TABLE 1

| Compound | Walnut Basal Medium Concentration Range | Preferred Concentration (mg/L) |
|---|---|---|
| $NH_4NO_3$ | 1300–1500 | 1416.0 |
| $Ca(NO_3)_2.4H_2O$ | 1800–2200 | 1968.0 |
| $Zn(NO_3)_2$ | 15–20 | 17.0 |
| $K_2SO_4$ | 1400–1700 | 1559.0 |
| $MgSO_4.7H_2O$ | 700–800 | 740.0 |
| $MnSO_4.4H_2O$ | 30–40 | 33.5 |
| $CuSO_4.5H_2O$ | 0.0–1.0 | 0.25 |
| $NiSO_4.6_2O$ | 0.0–0.01 | 0.00533 |
| $CaCl_2.2H_2O$ | 100–200 | 149.0 |
| $KH_2PO_4$ | 200–300 | 265.0 |
| $H_3BO_3$ | 1–10 | 4.8 |
| $Na_2MoO_4$ | 0.0–1.0 | 0.39 |
| $FeSO_4.7H_2O$ | 10–100 | 33.8 |
| $Na_2$ EDTA | 10–100 | 45.4 |
| Thiamine HCl | 0–10 | 2.0 |
| Nicotinic Acid | 0–10 | 1.0 |
| Glycine | 0–10 | 2.0 |
| Inositol | 50–200 | 100.0 |
| Sucrose | 25–35 g/L | 30 g/L |
| Gelrite ® | 2.0–2.5 g/L | 2.05 g/L |
| pH | 5.0–6.0 g/L | 5.5 |

For peach propagules, a suitable method for tissue culture of mature plant materials is as follows. Single or multiple nodal explants are placed for approximately one week on an optimum basal medium without hormones (see formulation below). Single node explants are then cultured individually in the basal medium supplemented with approximately 0.15 to 0.2 mg/L BA and about 0.002 mg/L IBA, and multiplication cultures are formed as described above for walnut. Such tissue culture results in multiple shoot formation, providing the propagules which are the starting material of the method of the present invention.

TABLE 2

| Compound | Peach Basal Medium Concentration Range | Preferred Concentration (mg/L) |
|---|---|---|
| $NH_4NO_3$ | 5000–6000 | 5592.9 |
| $Ca(NO_3)_2.4H_2O$ | 2500–3500 | 3049.0 |
| $Zn(NO_3)_2$ | 20–60 | 39.9 |
| $K_2SO_4$ | 600–800 | 698.6 |
| $MgSO_4.7H_2O$ | 400–700 | 546.8 |
| $MnSO_2.4H_2O$ | 50–70 | 66.5 |
| $CuSO_4.5H_2O$ | 0.0–1.0 | 0.25 |
| $NiSO_4.6H_2O$ | 0.0–0.01 | 0.00459 |
| $CaCl_2.2H_2O$ | 100–200 | 131.6 |
| $KH_2PO_4$ | 500–1000 | 822.0 |
| $H_3BO_3$ | 1.0–25.0 | 10.07 |
| $Na_2MoO_4$ | 0.0–1.0 | 0.39 |
| $FeSO_4.7H_2O$ | 10–100 | 33.8 |
| $Na_2$ EDTA | 10–100 | 45.4 |
| Thiamine HCl | 0.0–10 | 1.08 |
| Inositol | 0.0–10 | 1.0 |
| Sucrose | 25–35 g/L | 30 g/L |
| Agar | 8.0–9.0 g/L | 8.5 g/L |
| pH | 5.0–6.0 | 5.5 |

Once suitable propagules are obtained by any of the above-described methods, the propagules are transferred to a pretreatment medium under conditions which encourage lignification and hardening of the propagule prior to root emergence. The exact nature of the treatment will vary depending on the species of the plant, but will involve an alteration of the amounts of available nutrients, a gradual increasing of light intensity, and a gradual reduction of the surrounding temperature. The alteration of available nutrients typically comprises a decrease in nitrogen of at least 50%, more usually at least 75%, based on the available nitrogen in the multiplication medium, and an increase in sugar concentration, particularly sucrose concentration, of at least 25%, more usually at least 50%, based on the sucrose in the multiplication medium. The nutrient variation results in hardening of the propagule, which is further encouraged by the variations in light and temperature. Moreover, it is believed that the increse in sucrose results in enhanced root formation when the propagule is planted in the field after root induction. The total pretreatment time required will vary depending on the plant species, usually being in the range from three days to two weeks, more usually being about one week, and can best be determined by observing the survival rate of the propagules when planted in the field, as will be discussed below.

For the Paradox walnut, a suitable pretreatment medium is the walnut basal medium (Table 1) having the following modifications:

| Compound | Concentration Range | Preferred Concentration | Change* |
|---|---|---|---|
| Sucrose | 40-60 g/L | 53 g/L | +75% |
| IBA | 0.1-0.2 mg/L | 0.15 mg/L | +1500%** |
| $NH_4NO_3$ | 400-500 mg/L | 452.2 mg/L | −68% |
| $Ca(NO_3)_2$ | 600-700 mg/L | 634.0 mg/L | −68% |

*based on preferred basal medium
**based on supplemented basal medium.

The Gelrite ® (Kelco, Inc.) concentration in the medium is gradually increased from 2 g/l to about 2.5 g/l, preferably 2.1 g/l to 2.4 g/l, over the pretreatment period. The light intensity is increased from about 50 $\mu Es^{-1}m^{-2}$ to about 70 $\mu Es^{-1}m^{-2}$, while the day length is decreased from 24 hours to 17 hours. The temperature is lowered from about 30° C. to about 18°-22° C., usually about 19° C., and the pretreatment period lasts about a week.

For peach trees, a suitable pretreatment medium is the peach basal medium modified as follows:

| Compound | Concentration Range | Preferred Concentration | Change* |
|---|---|---|---|
| Sucrose | 60-80 g/L | 70 g/L | +133% |
| IBA | 5-15 mg/L | 10.0 mg/L | $+5 \times 10^5$%** |
| $NH_4NO_3$ | 1000-1500 mg/L | 1230 mg/L | −78% |
| $Ca(NO_3)_2$ | 600-750 mg/L | 670 mg/L | −78% |

*based on preferred basal medium.
**based on supplemented basal medium.

The agar concentration is increased from 8.5 to 9 g/l over the pretreatment period, and the light intensity, exposure time, and temperature are varied as described above for walnut. The pretreatment period is about one week.

The pretreatment step is critical to the successful propagation of tissue culture propagules according to the method of the present invention. It is the hardening of the tissue culture propagule and predisposition to root induction at this stage which allows survival of the propagule when it is transferred directly to the field, as will be described hereinafter.

After sufficient hardening of the propagule has been obtained, root formation is usually induced by exposing the hardened propagules to suitable root induction compounds, e.g., IBA, naphthaleneacetic acid (NAA), indolacetic acid (IAA), and the like. Typically, the propagule is dipped in the root induction compound (liquid or powder), and then placed directly in the field, or alternately in a suitable potting mix or equivalent synthetic media under high humidity conditions for a period of about one to two weeks, usually one week. Conveniently, a high density flat such as the Techniculture ® flat manufactured by Castle & Cooke, San Francisco, Calif., may be employed. It is not always necessary to separately expose the propagules to the root inducing compounds, however, and field planting may often be carried out directly after hardening pretreatment in a medium including root inducing compound(s) in an amount effective to induce root formation, usually at least 1 mg/L, often at least 10 mg/L IBA or equivalent. Separate exposure to the root induction compounds, however, will often promote even rooting and growth of the propagule after planting. In either case, the propagules are planted in the field prior to root emergence, typically from about 3 to 8 days from removal from the pretreatment medium, at which time the base of the propagule will be swollen with the preemergent roots. In this way, root formation occurs in the field rather than during an intermediate rooting stage, typically accomplished in a greenhouse.

Planting of the propagule in the field is accomplished in a conventional manner. The field soil may be cultivated, and soil amendments and fertilizers may be introduced according to well-known practices. After planting, the propagule must be maintained in an environment having elevated humidity, moderated temperature extremes, and reduced light intensity until the root system is established and the resulting plantlet has become acclimatized to the uncontrolled environment. Of these parameters, reduced light intensity is perhaps the most critical, with peak light intensity reduced by a factor in the range from 0.3 to 0.8, usually not exceeding 500 $\mu Es^{-1}m^{-2}$, more usually being below about 350 $\mu Es^{-1}m^{-2}$. It is also critical to maintain the propagule in a moist environment to avoid wilting. The length of time during which the planted propagule (plantlet) must be protected will vary depending on the species and the ambient conditions. Protection will always be continued until rooting has occurred, and usually for sometime thereafter. Typically, protection periods range from two to eight weeks, usually from three to six weeks.

The environmental control may be achieved most simply by covering the plantlet with a translucent moisture barrier which retains moisture around the plant, reduces the light intensity during the day, and lessens the extremes of temperature variation experienced by the propagule. Varying amounts of ventilation may be provided in the barrier to adjust the internal conditions to the desired levels. Proper irrigation of the propagule and resulting plantlet must also be provided. Frequent irrigation or the use of a drip irrigation system will provide the necessary water to the plants, which initially must be kept moist at all times.

Referring now to FIG. 1, the construction of a plant cover suitable for use with the method of the present invention is illustrated. A propagule P has been planted in the soil S and is illustrated sometime after planting after the emergence of roots and small leaves. The light and moisture barrier comprises a pair of nested cones, e.g., common plastic drinking cups 10 and 12. The inner cup 10 is composes of a high density plastic, such as polyvinyl-chloride, polyethylene terepthalate, polypropylene, or the like. The inner cup 10 may be clear plastic or may be translucent, depending on the amount of light intensity reduction required. The second cup 12 will usually be an expanded, cellular polystyrene such as that commonly available under the trade name Styrofoam (Dow Chemical Company, Midland, Mich.). The polystyrene cup will be translucent to provide for light intensity reduction and will have a relatively high thermal resistivity (R) to help insulate the plant from the environmental temperature extremes. The second cup 12 will be somewhat larger than the first cup 10 to provide an air space 14 between the two cups which also helps to insulate the propagule P from the environment. Ventilation hole 16 may be provided in the outer cup 12 to reduce the insulating effect if desired. Similar ventilation holes (not illustrated) may also be provided in the inner cup 10 for the same purpose. After planting the propagule P, the first plastic cup 10 is placed over the propagule and pressed down into the soil to provide a seal around the rim. The second cup 12 is then placed over the first cup 10 and similarly pressed into the soil. In some cases, it may be advantageous to place a third cup (not shown) over the cups 10 and 12 to further reduce light intensity. If desired, a drip irrigation line 18 may be inserted through the cups 10 and 12, as illustrated, or in the soil. Alternately, the cups can be removed for irrigation, or irrigation achieved by watering the soil around the cups. In any event, the cups are maintained over the propagule P and resulting plantlet until the plantlet has become sufficiently hardened to withstand the uncontrolled environment. Usually, the plantlets are left covered until their foilage completely occupies the volume of the first cup 10.

The following experiments are offered by way of illustration, not by way of limitation.

EXPERIMENTAL

Materials and Methods

1. Pretreatment

Pretreatment media were prepared by addition of varying amount of sucrose, indole-3-butyric acid (IBA), and nitrogen salts to the basal media described in Tables 1 and 2 above. Rapidly growing Paradox walnut shoots (3–10 cm) from multiple shoot cultures obtained as described by Driver and Kuniyuki, supra., were cut and the basal end placed in the modified media. Rapidly growing peach shoots (3–10 cm) were obtained by the method described above for peach propagation, and the shoots placed in the media in the same manner as the walnut shoots. The shoots were treated for varying times, and the effect of altering the IBA concentration, nitrogen salt concentration, and sucrose concentration in the pretreatment media on subsequent rooting was observed.

2. Root Induction

Root formation in the walnut propagules was induced by dipping the pretreated shoots in a 2% indole-3-butyric acid (IBA) powder (2 g IBA/100 g talc) leaving a thin layer of powder on the base. Peach propagules were rooted without a separate root induction treatment.

3. Rooting

The propagules were planted in high density trays (Techniculture ®, Castle & Cooke) in a Precival incubator (Percival, Ames, Iowa), with the temperature controlled at 19° C., the light intensity at 66 $\mu Es^{-1}m^{-2}$, and 17 hr. of light. All results reported were assessed 21 days after planting. In parallel experiments, it was found that propagules treated in accordance with the present invention which were able to successfully root in the high density trays in the growth room, were also able to root and grow in the field under the protected conditions described above.

Results

The effect of the length of the pretreatment period on the propagation of Paradox walnut shoots was assessed. Two replications of 144 shoots were treated for periods of 5, 15, 20, 35, and 50 days. The percentage of shoots which rooted, average number of roots per shoot, and length of the longest root were determined for each treatment group 21 days after root induction and planting. The results are summarized in Table 3.

TABLE 3

| Pretreatment[a,b] length (days) | No. roots | Length (cm) longest root | % Rooted | Value[c] |
| --- | --- | --- | --- | --- |
| 5 | 1.75 | 3.31 | 53 | 58.06 |
| 15 | 2.69 | 3.49 | 75 | 81.18 |
| 20 | 2.14 | 2.72 | 61 | 65.86 |
| 35 | 2.15 | 2.74 | 59.7 | 64.49 |
| 50 | 1.60 | 2.42 | 45.1 | 37.32 |

[a]Sucrose concentration = 30 g/L.
[b]IBA concentration = 0.01 m/L.
[c]Value = (No. roots + length + %).

The effect of length of pretreatment and sucrose concentration in the pretreatment media on walnut shoot rooting were also assessed. Groups of 72 Paradox walnut shoots were treated with sucrose concentrations ranging from 20 to 60 g/L, for periods of 7, 14, and 21 days. The results were determined 21 days after root induction and planting, and are summarized in Tables 4 and 5.

TABLE 4

| Pretreatment sucrose conc. (g/L) | No. roots | Length (cm) longest root | % Rooted | Value[b] |
| --- | --- | --- | --- | --- |
| 7 Day | Optimum concentration = 52.64 g/L | | | |
| 20 | 2.15 | 3.57 | 55.5 | 61.22 |
| 30 | 2.31 | 3.63 | 80.5 | 86.44 |
| 40 | 2.88 | 2.77 | 86.9 | 92.55 |
| 50 | 3.05 | 3.04 | 93.0 | 99.09 |
| 60 | 2.59 | 3.79 | 93.3 | 99.68 |
| 14 Day | Optimum concentration = 40.22 g/L | | | |
| 20 | 2.52 | 3.29 | 81.94 | 87.75 |
| 30 | 2.77 | 3.28 | 91.67 | 97.72 |
| 40 | 2.48 | 3.65 | 93.06 | 99.16 |
| 50 | 2.23 | 3.73 | 90.28 | 96.24 |
| 60 | 2.07 | 3.74 | 83.33 | 89.14 |
| 21 Day | Optimum concentration = N/A | | | |
| 20 | 3.04 | 2.18 | 86.66 | 91.88 |
| 30 | 3.01 | 2.70 | 81.48 | 87.19 |
| 40 | 3.19 | 2.16 | 91.18 | 96.53 |
| 50 | 3.09 | 2.78 | 84.62 | 90.49 |
| 60 | 3.85 | 3.05 | 91.89 | 98.79 |

[a]IBA concentration = 0.01 mg/L.
[b]Value = (No. roots + length + %)

TABLE 5

| Pretreatment length (days) | No. roots | Length (cm) longest root | % Rooted | Value[b] |
| --- | --- | --- | --- | --- |
| 20 g/L Sucrose | Optimum No. of Days = 19 | | | |
| 7 | 2.15 | 3.57 | 55.50 | 61.22 |
| 14 | 2.52 | 3.29 | 81.94 | 87.75 |
| 21 | 3.04 | 2.18 | 86.66 | 91.88 |
| 30 g/L Sucrose | Optimum No. of Days = 14 | | | |
| 7 | 2.31 | 3.63 | 80.50 | 86.44 |
| 14 | 2.77 | 3.28 | 91.67 | 97.72 |
| 21 | 3.01 | 2.70 | 81.48 | 87.19 |

TABLE 5-continued

| Pretreatment length (days) | No. roots | Length (cm) longest root | % Rooted | Value[b] |
|---|---|---|---|---|
| 40 g/L Sucrose Optimum No. of Days = 15 | | | | |
| 7 | 2.88 | 2.77 | 86.90 | 92.55 |
| 14 | 2.48 | 3.65 | 93.06 | 99.16 |
| 21 | 3.19 | 2.16 | 91.18 | 96.53 |
| 50 g/L Sucrose Optimum No. of Days = 4 | | | | |
| 7 | 3.05 | 3.04 | 93.00 | 99.09 |
| 14 | 2.23 | 3.73 | 90.28 | 96.24 |
| 21 | 3.09 | 2.78 | 84.62 | 90.49 |
| 60 g/L Sucrose Optimum No. of Days = N/A | | | | |
| 7 | 2.59 | 3.79 | 93.30 | 99.68 |
| 14 | 2.07 | 3.74 | 83.33 | 89.14 |
| 21 | 3.85 | 3.05 | 91.89 | 98.79 |

[a]IBA concentration = 0.01 mg/L.
[b]Value = (No. roots + length + %)

The effect of varying the concentration of IBA in the pretreatment media was assessed. Groups of 36 Paradox walnut shoots were treated with IBA concentrations ranging from 0 to 0.1 mg/L. The results are summarized in Table 6. A similar experiment was run on groups of 72 Paradox walnut shoots, and the results are presented in Table 7.

TABLE 6

| Pretreatment IBA conc. (mg/L) | No. roots | Length (cm) longest root | % Rooted | Value[a] |
|---|---|---|---|---|
| Sucrose concentration = 52.64 g/L Treatment time = 7 days | | | | |
| 0 | 2.25 | 3.69 | 90.51 | 96.45 |
| 0.001 | 2.45 | 3.63 | 94.44 | 100.52 |
| 0.003162 | 2.59 | 3.51 | 87.50 | 93.60 |
| 0.01 | 2.31 | 3.79 | 87.50 | 93.60 |
| 0.03162 | 3.40 | 3.97 | 95.80 | 103.20 |
| 0.1 | 3.22 | 4.05 | 100.00 | 107.27 |
| Sucrose concentration = 40.22 g/L Treatment time = 14 days | | | | |
| 0 | 2.91 | 3.43 | 88.66 | 95.00 |
| 0.001 | 2.99 | 3.17 | 83.33 | 89.49 |
| 0.003162 | 2.91 | 3.32 | 88.89 | 95.12 |
| 0.01 | 2.65 | 3.35 | 95.84 | 101.84 |
| 0.03162 | 2.85 | 3.91 | 94.44 | 101.20 |
| 0.1 | 3.65 | 3.55 | 95.84 | 103.04 |

[a]Value = (No. roots + length + %)

TABLE 7

7 Day Sucrose concentration = 52.64 g/L

| Pretreatment[a] IBA conc. (mg/L) | No. roots | Length (cm) longest root | % Rooted | Value |
|---|---|---|---|---|
| 0 | 2.47 | 3.15 | 81.43 | 87.05 |
| 0.01 | 2.60 | 3.40 | 90.28 | 96.28 |
| 0.03162 | 2.63 | 3.22 | 93.06 | 98.91 |
| 0.1 | 3.09 | 3.50 | 93.06 | 99.65 |
| 3.162 | 3.64 | 3.55 | 93.06 | 100.25 |
| 10 | 3.14 | 3.30 | 90.28 | 96.72 |

[a]Value = (no. roots + length + %)

The effect of nitrogen concentration in the medium on the propagation of walnut shoots was assessed. Groups of 36 walnut shoots were treated with nitrogen in concentrations, varied by adjusting the level of nitrogen salts added to the medium. The results are summarized in Table 8.

TABLE 8

| Pretreatment Nitrogen conc.[b] (log value/L) | No. roots | Length (cm) longest root | % Rooted | Value[a] |
|---|---|---|---|---|
| Sucrose concentration = 52.64 g/L Treatment time = 7 days | | | | |
| None | 2.67 | 3.31 | 84.38 | 90.36 |
| 0.1 | 2.69 | 3.65 | 91.67 | 98.01 |
| 0.5 | 3.03 | 3.45 | 94.44 | 100.92 |
| 1.0 | 2.77 | 4.09 | 86.11 | 92.97 |
| 1.5 | 2.60 | 4.22 | 55.55 | 62.37 |
| 2.0 | 1.00 | .70 | 5.55 | 7.25 |
| Sucrose concentration = 40.22 g/L Treatment time = 14 days | | | | |
| None | 2.11 | 2.37 | 75.00 | 79.48 |
| 0.1 | 2.56 | 2.75 | 75.00 | 80.31 |
| 0.5 | 2.88 | 3.20 | 91.67 | 97.75 |
| 1.0 | 2.86 | 4.26 | 97.22 | 104.34 |
| 1.5 | 3.08 | 3.93 | 33.33 | 40.34 |
| 2.0 | 0 | 0 | 0 | 0 |

[a]Value = (No. roots + length + %)
[b]Nitrogen concentration was calculated as follows. "A" stock concentration (100X) NH$_4$NO$_3$ = 141.6 g/L; CA(NO$_3$)$_2$ = 196.8 g/L. Log value/L = the log of the volume in ml. from the group stock "A" (100X). 2.0 = ml/L; 1.5 = 31.62 ml/L; 1.0 = 10 ml/L; 0.5 = 3.162 ml/L; 0.1 = 0.1 ml/L.

The effect of varying the sucrose concentration in the pretreatment medium on the propagation of peach shoots was assessed. The data set forth in Table 9 are means of 24 values from one replication of the experiment expressed on the basis of a single shoot.

TABLE 9

| Pretreatment[a,b] Sucrose conc. (g/L) | No. roots | Length (cm) longest root | % Rooted | Value[c] |
|---|---|---|---|---|
| 10 | 2.00 | 4.55 | 17.4 | 23.95 |
| 20 | 2.25 | 4.48 | 33.3 | 40.03 |
| 30 | 3.34 | 5.00 | 45.8 | 53.88 |
| 40 | 4.13 | 5.71 | 33.3 | 43.14 |
| 50 | 2.64 | 5.83 | 45.8 | 54.27 |
| 60 | 5.45 | 5.39 | 45.8 | 56.64 |
| 70 | 3.33 | 6.56 | 75.0 | 84.89 |

[a]Seven day pretreatment period.
[b]IBA concentration = 0.002.
[c]Value = (no. roots + length + %).

The effect of varying the IBA concentration in the pretreatment medium on the propagation of peach shoots was assessed. The data set forth in Table 10 are means of 36 values from one replication of the experiment. No separate root induction step was performed.

TABLE 10

| Pretreatment[a,b] IBA conc. (mg/L) | No. roots | Length (cm) longest root | % Rooted | Value[c] |
|---|---|---|---|---|
| 0 | 2.33 | 3.96 | 66.67 | 72.96 |
| 0.01 | 4.13 | 4.70 | 66.67 | 75.50 |
| 0.03162 | 1.80 | 4.84 | 41.66 | 48.30 |
| 0.1 | 2.33 | 2.63 | 75.00 | 79.96 |
| 3.162 | 4.00 | 4.15 | 50.00 | 58.15 |
| 10. | 3.92 | 5.36 | 100.00 | 109.28 |

[a]Seven day pretreatment period.
[b]Sucrose concentration = 70.0 g/L.
[c]Value = (No. roots + length + %).

The effect of varyng the nitrogen concentration in the pretreatment medium on propagation of peach shoots was assessed. The data set forth in Table 11 are means of 48 values from one replication of the experiment expressed on the basis of a single shoot.

TABLE 11

| Nitrogen[a,b,c] conc. (log value/L) | No. roots | Length (cm) longest root | % Rooted | Value[d] |
|---|---|---|---|---|
| 0 | 7.27 | 6.32 | 91.66 | 105.25 |
| 0.1 | 8.00 | 5.90 | 100.00 | 113.90 |
| 0.5 | 6.45 | 6.26 | 91.66 | 104.37 |
| 1.0 | 6.00 | 6.05 | 75.00 | 87.05 |
| 1.5 | 0 | 0 | 0 | 0 |

[a]Sucrose concentration = 70.0 g/L.
[b]IBA concentration = 10 g/L.
[c]Nitrogen concentration is defined in Table 7.
[d]Value = (No. roots + length + %).

Although the foregoing invention has been described in some detail by way of illustration and example for purposes of clarity of understanding, it will be obvious that certain changes and modifications may be practiced within the scope of the appended claims.

What is claimed is:

1. A method for propagating plant shoots, said method comprising:
    multiplying the shoots in a multiplication culture having preselected levels of sugar and available nitrogen to yield a plurality of propagules;
    maintaining individual propagules obtained from the multiplication culture on a pretreatment medium for a predetermined time period, said pretreatment medium characterized by elevated sugar levels and reduced nitrogen levels relative to those in the multiplication medium;
    exposing the propagules to at least one root inducing compound at a concentration sufficient to induce root formation; and
    planting the root-induced propagules prior to root emergence directly in a field under a translucent moisture barrier which confers light and humidity conditions selected to allow gradual acclimatization of a resulting plantlet to ambient conditions, whereby initial root formation of the plantlet occurs in the field.

2. A method as in claim 1, wherein the propagules are maintained in the pretreatment medium for at least three days prior to exposure to the root inducing compound.

3. A method as in claim 1, wherein the propagules are exposed to the root inducing compound as a part of the pretreatment medium.

4. A method as in claim 1, wherein the pretreatment culture is maintained with increased light intensity relative to the multiplication culture.

5. A method as in claim 1, wherein the pretreatment culture is maintained with decreased temperature relative to the multiplication culture.

6. A method as in claim 1, wherein the root inducing medium is a solid medium.

7. A method as in claim 1, wherein the root inducing compound is in the form of a powder.

8. A method as in claim 1, wherein the root induced propagules are planted in the field substantially immediately after root induction.

9. A method as in claim 1, wherein the propagules are dipped in the root inducing at least one compound and placed in a rooting medium under controlled environmental conditions for a preselected period prior to planting in the field.

10. A method as in claim 1, wherein the translucent moisture barrier reduces light intensity by a factor in the range from 0.3 to 0.8.

11. A method as in claim 1, wherein the translucent moisture barrier comprises a pair of nested cones, where one cone is formed from a high density plastic and the other cone is formed from a low density plastic.

12. A method as in claim 1, wherein the plant shoots are woody plant shoots.

13. A method as in claim 12, wherein the woody plant shoots are dicotyledons.

14. A method as in claim 13, wherein the dicotyledons are gymnosperms.

15. A method as in claim 13, wherein the dicotyledons are angiosperms.

16. A method as in claim 1, wherein the sugar level in the pretreatment medium is increased by at least 25% and the nitrogen level is decreased by at least 50%.

17. A method as in claim 16, wherein the sugar is sucrose, and the nitrogen is one or more nitrogen salt.

18. A method as in claim 17, wherein the nitrogen salts are selected from a group consisting of ammonium nitrate and calcium nitrate.

19. A method for propagating plant shoots, said method comprising:
    multiplying the shoots in a multiplication culture having preselected levels of sugar and available nitrogen to yield a plurality of propagules;
    maintaining individual propagules obtained from the multiplication culture on a pretreatment medium for a predetermined time period, said pretreatment medium characterized by elevated sugar levels and reduced nitrogen levels relative to those in the multiplication medium;
    exposing the propagules to at least one root inducing compound at a concentration sufficient to induce root formation; and
    planting the root-induced propagules prior to root emergence in a field under a translucent moisture barrier which reduces light intensity by a factor in the range from 0.3 to 0.8 to confer controlled light and humidity conditions selected to allow gradual acclimatization of a resulting plantlet to ambient conditions, whereby initial root formation of the plantlet occurs in the field.

20. A method as in claim 19, wherein the translucent moisture barrier comprises a pair of nested cones, where one cone is formed from a high density plastic and the other cone is formed from a low density plastic.

21. A method for propagating peach tree shoots, said method comprising:
    multiplying peach tree propagules in a multiplication culture having a maximum sucrose concentration of 35 g/L and minimum nitrogen salt concentration of 7500 mg/L;
    maintaining individual propagules obtained from the multiplication culture on a pretreatment medium for a preselected time period, said pretreatment medium having a minimum sucrose concentration of 60 g/L, and a maximum nitrogen salt concentration of 2250 mg/L;
    exposing the propagules to at least one root inducing compound at a concentration sufficient to induce subsequent root formation; and
    planting the peach propagule directly in the field under a translucent moisture barrier prior to root emergence.

22. A method as in claim 21, wherein the root inducing compound is present in the pretreatment medium.

23. A method as in claim 22, wherein the preselected treatment period is one week.

24. A method as in claim 22, wherein the translucent light and moisture barrier reduces light intensity by a factor in the range from 0.3 to 0.8.

25. A method for propagating Paradox walnut shoots, said method comprising:

multiplying Paradox walnut propagules in a multiplication culture having a maximum sucrose concentration of 35 g/L and a minimum salt concentration of 2100 mg/ml;

maintaining individual propagules obtained from the multiplication culture on a pretreatment medium for a preselected time period, said pretreatment medium having a minimum sucrose concentration of 40 g/L, and a maximum nitrogen salt concentration of 1200 mg/L;

exposing the propagules to at least one root inducing compound after said preselected time period and at a concentration sufficient to induce subsequent root formation; and planting the walnut propagules directly in the field under a translucent moisture barrier prior to root emergence.

26. A method as in claim 25, wherein the preselected pretreatment period is one week.

27. A method as in claim 25, wherein the walnut propagules are exposed to the root inducing compound(s) by dipping the propagules in the compound(s).

28. A method as in claim 25, wherein the translucent light and moisture barrier reduces light intensity by a factor in the range from 0.3 to 0.8.

* * * * *